United States Patent [19]

Shtohryn et al.

[11] Patent Number: 4,820,523

[45] Date of Patent: Apr. 11, 1989

[54] PHARMACEUTICAL COMPOSITION

[75] Inventors: Liudoslava V. Shtohryn, Budd Lake; David Peters, Long Valley, both of N.J.

[73] Assignee: Warner-Lambert Company, Morris Plains, N.J.

[21] Appl. No.: 852,471

[22] Filed: Apr. 15, 1986

[51] Int. Cl.$^4$ .......................... A61K 9/22; A61K 9/26
[52] U.S. Cl. .................................. 424/469; 424/468; 424/470
[58] Field of Search ........................ 424/468, 469, 470

[56] References Cited

U.S. PATENT DOCUMENTS

| | | | |
|---|---|---|---|
| 2,993,836 | 7/1961 | Nash et al. | 424/470 |
| 3,062,720 | 11/1962 | Costello | 424/469 |
| 3,400,197 | 9/1968 | Lippman | 424/469 |
| 3,402,240 | 9/1968 | Cain et al. | 424/469 |
| 3,577,514 | 5/1971 | Robinson | 424/468 |
| 4,483,847 | 11/1984 | Augart | 424/470 |
| 4,552,899 | 12/1985 | Sunshine et al. | 514/568 |
| 4,581,232 | 4/1986 | Peters et al. | 424/155 |
| 4,590,062 | 5/1986 | Jang | 424/469 |
| 4,619,934 | 10/1986 | Sunshine et al. | 514/290 |
| 4,632,821 | 12/1986 | Peters et al. | 424/155 |
| 4,642,231 | 10/1987 | Peters et al. | 424/155 |
| 4,643,892 | 2/1987 | Peters et al. | 424/155 |
| 4,647,450 | 3/1987 | Peters et al. | 424/155 |
| 4,650,663 | 3/1987 | Peters et al. | 424/155 |
| 4,704,284 | 11/1987 | Beatty et al. | 424/469 |
| 4,747,881 | 5/1988 | Shaw et al. | 424/476 |
| 4,752,485 | 6/1988 | Sharma et al. | 426/99 |
| 4,753,800 | 6/1988 | Mozda | 424/440 |

Primary Examiner—Shep K. Rose
Attorney, Agent, or Firm—Gary M. Nath; Charles A. Gaglia, Jr.

[57] ABSTRACT

Pharmaceutical composition of matter for use in the treatment of sinus, allergy, and cold symptoms, which comprises an effective amount of a pharmaceutically acceptable salt of phenindamine entrapped in a leachable non-toxic wax matrix in combination with at least one analgesic, decongestant, antitussive, and mixtures thereof.

10 Claims, No Drawings

PHARMACEUTICAL COMPOSITION

This invention relates to a pharmaceutical composition of matter for use in the treatment of sinus, allergy and cold symptoms and more particularily to the preparation and use of a leachable non-toxic wax matrix containing pharmaceutically acceptable salts of phenindamine.

Phenindamine (2,3,4,9-Tetrahydro-2-methyl-9-phenyl-1H-indeno[2,1-c]pyridine) is a stable, white crystalline powder described in 1949 in U.S. Pat. No. 2,470,108. The tartrate salt is soluble up to 3% in water, and sparingly soluble in propylene glycol. Unlike other antihistamines in common use, phenindamine does not produce drowsiness and sleepiness and on the contrary has a mild stimulating action on some patients and may even cause insomnia when taken before bedtime. The use of phenindamine, however, has been curtailed because of its inadequate antihistamine properties. This may have been due to its isomerization to an inactive form, isophenindamine. The isomerization reaction has been found to occur when phenindamine is stored in both wet and dry states and is enhanced in solutions having an alkaline pH or when formulated with oxidizing substances. Commercial formulations containing phenindamine include Nolahist and Nolamine (both trademarks of Carnrick Laboratories).

Nolahist is a film coated tablet containing 25 mg of phenindamine tartrate formulated for temporary relief of running nose, sneezing and watery eyes whereas Nolamine is a film coated tablet containing 24 mg phenindamine tartrate, 4 mg chlorpheniramine maleate, and 50 mg phenylpropanolamine hydrochloride formulated to provide 8 to 12 hours of continuous relief.

A need exists for a nonsedating, and yet mild, antihistamine product which is storage stable for long periods of time even when phenindamine is used in the presence of alkaline buffers and known oxidizing agents.

Various attempts have been made to entrap pharmaceutically active ingredients to enable the formation of sustained release formulations and formulations that dissolve or erode in the gastrointestinal tract.

U.S. Pat. No. 3,402,240 describes a tablet which is useful in administrating many therapeutic agents and drugs some of which, for illustrative purposes, are organic nitrites, sympathomimetic amines, barbituric acid derivatives, salicylates, xanthine derivatives, and many others. The tablet comprises a matrix substantially insoluble in gastric and intestinal juices, a therapeutically bland or inert filler or extender and an active therapeutic agent or drug. The matrix is constituted of such materials as carnauba wax, candelilla wax, esparto wax, or ouricury wax, which have melting points between about 68° and 90° C.

The filler or extender may be any one of the standard materials used in making medicinal tablets, such as calcium or sodium phosphate dibasic, magnesium stearate (serving also as a lubricant in tableting), calcium phosphate tribasic, talc, calcium oxide, calcium stearate, sodium stearate and starch and mixtures thereof as now used in the making of tablets and methylcellulose (serving also as a swelling agent in the gastrointestinal tract).

U.S Pat. No. 2,875,130 discloses a method of preparing a sustained release pharmaceutical powder which comprises reducing a solid medicament to a particle size of a maximum of about 10 microns, mixing the thus formed particles in from about 5% to about 35% by weight of a liquefied lipid material which is substantially water insoluble and has a melting point of above about 85° C., solidifying the thus formed mixture and then reducing the solidified mixture to form a primary powder having a maximum particle size in the range of from about 5 to 25 microns. The thus formed powder is mixed with a melt of from about 25% to about 85% by weight of a lipid material which is substantially water insoluble and has a melting point which is a minimum of about 5° C. lower than the melting point of the first mentioned lipid material while maintaining the temperature of the melt below the melting point of the first mentioned lipid material and above the melting point of the second mentioned lipid material, mixing the powder-lipid mixture with water to form an emulsion while maintaining the water-powder-lipid mixture at a temperature above the melting point of the second mentioned lipid material and below the melting point of the first mentioned lipid material, cooling the emulsion to a temperature below the melting point of the second mentioned lipid material to precipitate the sustained release pharmaceutical powder, said solid medicament having a melting point higher than the second mentioned lipid material.

U.S. Pat. No. 4,552,899 discloses pharmaceutical compositions and methods of using same comprising a non-steroidal anti-inflammatory drug in combination with at least one other active component selected from an antihistamine, decongestant, cough suppressant (antitussive) or expectorant which are provided for the relief of cough, cold and cold-like symptoms.

Unlike the prior art systems a pharmaceutical composition has been unexpectedly discovered for use in the treatment of sinus, allergy, and cold symptoms which comprises an effective amount of a pharmaceutically acceptable salt of phenindamine entrapped in a leachable non-toxic wax matrix with at least one material selected from the group consisting of analgesics, decongestants, antitussives and mixtures thereof. The formulations of this invention provide for the virtual immediate release of phenindamine so that within 1 hour over 70% of the drug is dissolved out of the wax matrix. In addition, it has been found that by using the leachable non-toxic wax matrix of this invention virtually no isomerization of the active component occurs even in the presence of known isomerization agents, such as some of the analgesics and decongestants used in the formulations of this invention.

The compositions of this invention employ a phenindamine salt entrapped within a leachable non-toxic wax matrix. The matrix is substantially insoluble in gastric and intestinal juices yet rapidly releases the drug in the presence of the same. The matrix contains the phenindamine salt and an inert filler or extender as the leachable component of the matrix. When the matrix passes into the intestinal tract the surface of the matrix is attacked and the filler becomes leached out of or swells within the matrix particles rendering the drug available for therapeutic action. As the gastrointestinal juices continue to attack the filler and leach out the active component, the matrix begins to disintegrate. The leaching process should occur quite rapidly preferably within one hour to result in the release of at least 70% of the phenindamine. In order to provide for this rapid release, the amount of matrix, leachable component and phenindamine present must be carefully controlled.

The phenindamine is used as its pharmaceutically acceptable salt. Such salts may be selected from a wide range of materials and includes salts from the group consisting of citrate, hydrobromide, hydrochloride, maleate, succinate, sulfate, tartrate, and mixtures thereof. Phenindamine tartrate is the preferred active form of the drug. The amount of phenindamine used in the total formulation will depend on the dosage desired which may range from 12.5 to 50 mg. This amount may be provided by employing from about 4 to 40% by weight phenindamine in the wax matrix.

As discussed above, the delivery rate is effected by the quantity of the wax coating applied to the phenindamine coupled with the leachable component. It has been found necessary to employ at least one part wax for each part of phenindamine used to obtain sufficient stability of the drug, that is to avoid isomerization of phenindamine to isophenindamine. In addition it is also useful to not employ amounts above about 3 parts wax for each part phenindamine since such high amounts of wax result in delayed release of the drug. The wax matrix must be composed of materials having a melting point above about 35° C. and preferably from 50° to 90° C. Waxes having lower melting points hinder subsequent granulation/milling and/or tabletting procedures by causing sticking to the punch surfaces. Exemplary wax material include hydrogenated vegetable oil, beeswax, caranuba wax, paraffin, candelillia, ozokerite and mixtures thereof. It is also possible to employ other higher melting point waxes along with the lower melting point waxes described provided the final blend has a melting point within the desired range. The wax is preferably employed in the matrix in an amount of about 36 to 60% by weight of the total matrix. It should be recognized that the wax functions by protecting the phenindamine from being contacted with its isomerization agents present in the formulation, such as other drugs in the formulation or processing aids such as glidants and excipients.

Besides this function, the wax should be able to provide pathways for drug release. When high amounts of wax are employed these pathways are curtailed and fail to result in proper drug release.

The leachable component used in the matrix must be inert to phenindamine, that is does not promote its isomerization to isophenindamine. In addition the material must be either water swellable or water soluble so that when present in the gastrointestinal tract it disturbs the wax matrix so the drug is leached from the matrix. This disruption may occur by solubilization creating additional passages for the drug to be quickly released and/or by swelling causing disintegration of the wax matrix. Without being limited thereto exemplary materials include calcium sulfate, calcium carbonate, calcium phosphate (dibasic), sugar, starch and mixtures thereof. Materials that cannot be used include talc, hydroxypropylcellulose, modified starches, cellulose and microcrystalline cellulose. When employed in the matrix the leachable component is used in amounts of about 10 to about 60% by weight of the matrix.

The wax matrix is prepared by melting the wax and while mixing blending into the melted wax the leachable component and the phenindamine salt. The filler and drug may be added separately or simultaneously and may be added in portions or all at once. Once a homogenous mixture is obtained the mass is cooled, granulated and milled to produce a free flowing particulate material having an average particle size of about 125 to 425 microns. It should be recognized that the mixture does not need to be milled but may be used in a coarser condition.

In the pharmaceutical compositions and methods of the present invention the foregoing active ingredients will be combined with analgesic, decongestant, and antitussive materials. Nonlimiting illustrative examples include analgesic materials selected from the group consisting of acetaminophen, aspirin, salicylamide, phenacetin, ibuprofin and mixtures thereof, decongestant materials selected from phenylephrine hydrochloride, phenylpropanolamine, pseudoephedrine hydrochloride, ephedrine sulfate and mixtures thereof, and antitussive materials selected from dextromethorphan, dextromethorphan hydrobromide, noscapine, carbetapentane citrate, chlophedianol hydrochloride and mixtures thereof.

The formulations once prepared may be put into capsules, compressed into tablets, stored for future use or formulated with conventional carriers, to prepare pharmaceutical compositions which offer a variety of administration and dosages suitable for particular applications. Such compositions may be in the form of a lozenge, tablet, toffee, nougat, chewy candy, chewing gum, and so forth. The carriers may be selected from a wide range of materials. Without being limited thereto, such materials include bulking agents such as fillers, diluents, binders and adhesives, lubricants, disintegrants, colorants, flavorings, sweeteners and miscellaneous materials such as buffers and adsorbents in order to prepare a particular pharmaceutical composition. The preparation of confectionery and chewing gum products is historically well known and has changed very little over the years.

Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0 5 to 1.5% moisture. Such materials normally contain up to 92% corn syrup, up to 55% sugar and from 0.1% to 5.0% water. The syrup component generally is prepared from corn syrups high in fructose, but may include other materials. Further ingredients such as flavorings, sweeteners, acidulents, colorants and so forth may also be added.

Boiled candy lozenges may also be prepared from nonfermentable sugars such as sorbitol, mannitol, and hydrogenated corn syrup. A typical hydrogenated corn syrup is Lycasin (trademark of Roquette Feres). The candy lozenges may contain up to about 95% sorbitol, a mixture of sorbitol and mannitol at a ratio of about 9.5 to 0.5 up to about 7.5 to 2.5 and hydrogenated corn syrup up to about 55% of the syrup component.

In contrast, compressed tablet lozenges contain particular materials and are formed into structures under pressure. They generally contain sugars in amounts up to 95% and typical tablet excipients such as binders and lubricants as well as flavors, colorants and so forth.

The lozenges may be made of soft confectionary materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7g/cc.

By comparison, the high boiling syrup, or "bob syrup," is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, *CHOCOLATE, COCOA AND CONFECTIONERY: Science and Technology*, 2nd edition, AVI Publishing Co., Inc., Westport, Conn., (1980), at pages 424-425.

Tablets of this invention may also be in chewable form. This form is particularly advantageous because of convenience and patient acceptance and rapid onset of bioactivity. To achieve acceptable stability and quality as well as good taste and mouth feel several considerations are important, namely amount of active substance per tablet, flavor, compressibility and organoleptic properties of the drug.

The preparation of chewable medicated candy is prepared by procedures similar to those used to make soft confectionary. This procedure generally involves the formation of a boiled sugar-corn syrup blend to which is added a frappe mixture. The boiled sugar-corn syrup blend may be prepared from sugar and corn syrup blended in parts by weight ratio of 90 to 10:10 to 90. This blend is heated to temperatures above 250° F. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge like mass. The frappe is then added to the molten candy base and mixed until homogenous at temperatures between 150° F. and 250° F. The leachable wax matrix can then be added as the temperature of the mix is lowered to around 120° F. to 194° F. whereupon additional ingredients are added such as flavors, and colorants. The formulation is further colled and formed to pieces of desired dimensions.

A general discussion of the lozenge and chewable tablet forms of confectionery may be found in H. A. Lieberman. and L. Lachman. *Pharmaceutical Dosage Forms: Tablets* Volume 1, Marcel Dekker, Inc., New York, N.Y. at pages 289 to 466, incorporated herein by reference.

With regard to the chewing gum formulation in particular, the amount of gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene and polyvinylacetate and mixtures thereof, are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hyrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alphapinene or betapinene; terpene resins including polyterpene and mixtures thereof. The solvent may be employed in an amount ranging from about 10% to about 75% and preferable about 45% to about 70% by weight to the gum base.

A variety of traditional ingredients such as plasticizers or softeners such as lanolin, stearic acid, sodium stearate, potassium stearate, glyceryl triacetate, glycerine and the like for example, natural waxes, petroleum waxes, such as polyurethene waxes, paraffin waxes and microcrystalline waxes may also be incorporated into the gum base to obtain a variety of desirable textures and consistency properties. These individual additional materials are generally employed in amounts of up to about 30% by weight and preferably in amounts of from about 3% to about 20% by weight of the final gum base composition.

The chewing gum composition may additionally include the conventional additives of flavoring agents, coloring agents such as titanium dioxide; emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts, Preferably the amount of fillers when used will vary from about 4% to about 30% by weight of the final chewing gum.

In the instance where auxiliary sweeteners are utilized, the present invention contemplates the inclusion of those sweeteners well known in the art, including both natural and artificial sweeteners. Thus, additional sweeteners may be chosen from the following non-limiting list:

A. Water-soluble sweetening agents such as monosaccharides, disaccharides and polysaccharides such as xylose, ribose, glucose, mannose, galactose, fructose, dextrose, sucrose, sugar, maltose, partially hdryolyzed starch, or corn syrup solids and sugar alcohols such as sorbitol, xylitol, mannitol and mixtures thereof.

B. Water-soluble artificial sweeteners such as the soluble saccharin salts, i.e., sodium, or calcium saccharin salts, cyclamate salts, acesulfame-K and the like, and the free acid form of saccharin.

C. Dipeptide based sweeteners such as L-aspartyl-phenylalanine methyl ester and materials described in U.S. Pat. No. 3,492,131 and the like.

In general, the amount of sweetener will vary with the desired amount of sweeteners selected for a particular chewing gum. This amount will normally be 0.001% to about 90% by weight when using an easily extractable sweetener. The water-soluble sweeteners described in category A above, are preferably used in amounts of about 25% to about 75% by weight, and most preferably from about 50% to about 65% by weight of the final chewing gum composition. In contrast, the artificial sweeteners described in categories B and C are used in amounts of about 0.0005% to about 5.0% and most preferably about 0.05 to about 2.5% by weight of the final chewing gum composition. These amounts are ordinarily necessary to achieve a desired level of sweetness independent from the flavor level achieved from flavor oils. While water may be added independently with dry sweeteners, it will generally be added as part of a corn syrup or corn syrup mixture.

Suitable flavorings include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final composition weight.

The colorants useful in the present invention, include the pigments such as titanium dioxide, that may be incorporated in amounts of up to about 1% by weight, and preferably up to about 0.6% by weight. Also, the colorants may include other dies suitable for food, drug and cosmetic applications, and known as F.D. & C. dyes and the like. The materials acceptable for the foregoing spectrum of use are preferably water-soluble. Illustrative examples include indigoid die, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salt of 4-[4-Nethyl-p-sulfobenzylamino)diphenylmethylene]-[1-(N-ethyl-N-p-sulfoniumbenzyl)-2,5-cyclohexadienimine]. A full recitation of all F.D. C. and D. & C. and their corresponding chemical structures may be found in the Kirk-Othmer Encyclopedia of Chemical Technology, 3rd Edition in Volume 6, at pages 561-595, which text is accordingly incorporated herein by reference.

Suitable oils and fats that are useable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

The present invention is further illustrated by the following examples. All parts and percentages in the examples and throughout the specification and claims are by weight unless otherwise indicated.

EXAMPLE I

Inventive Runs 1 to 3

Comparative Runs A to H

This Example demonstrates the formation of several comparative and inventive formulations.

The formulations described in Table I were prepared by melting the wax and adding the remaining ingredients. The mixture was blended, cooled to approximately 25° C., granulated and milled to a particle size of 125 to 425 microns. The wax blends were stored at 80° C. and 25° C. for at least 16 hours before being assayed for phenindamine content.

The stability of the phenindamine was determined by HPLC assay (high performance liquid chromatography). No isomerization products were detected by the standard USP-XXI procedure. The percent phenindamine released from the wax blend was determined by placing 80 milligrams of powder blend into 80 milliliters of DI water at 37° C. and rotated at 40 rpm for 1 hour. The phenindamine content was determined by HPLC assay.

The results are set forth in Table I and indicate that the comparative runs produce a product that is either unstable or does not result in an effective release of phenindamine from the formulation.

The inventive runs all demonstrated good stability upon storage and released effective amounts of phenindamine, that is amounts above about 70%.

TABLE I

| Runs | % Wax | % Phenindamine | % Filler | Filler Used | Stable | (% Released) Dissolution |
| --- | --- | --- | --- | --- | --- | --- |
| Inventive 1 | 55 | 25 | 20 | Calcium Sulfate | Yes | 71.4 |
| Inventive 2 | 40 | 25 | 35 | Calcium Sulfate | Yes | 88.8 |
| Inventive 3 | 40 | 25 | 35 | Calcium Sulfate | Yes | 89.6 |
| Comparative A | 50 | 50 | — | — | Yes | <50 |
| Comparative B | 75 | 25 | — | — | Yes | <50 |
| Comparative C | 37.5 | 62.5 | — | — | No | * |
| Comparative D | 30 | 70 | — | — | No | * |
| Comparative E | 65 | 25 | 10 | Calcium Sulfate | ** | 55.0 |
| Comparative F | 65 | 25 | 10 | 6X Sugar | ** | 56.4 |
| Comparative G | 65 | 5 | 30 | 6X Sugar | ** | 51.9 |
| Comparative H | 65 | 25 | 10 | Bottler's Sugar | ** | 57.6 |

6X Sugar = Powdered Sugar with 3% Corn Starch
*Not required due to instability
**Not required due to unacceptable dissolution

EXAMPLE II

Comparative Runs I to V

This example demonstrates the formation of several comparative formulations with active ingredients.

The formulations described in Table II were either granulated with water until a uniformly wetted and free flowing granulation resulted (Comparative Runs I, J, K and M) or dry blended. (Comparative Runs L and N to V). The granulations and powder blends were stored and assayed as in Example I.

The results are set forth in Table II, and indicate that although a product may be stable with only phenindamine and a filler, this same product becomes unstable when other actives (APAP and/or Pseudoephedrine) are added.

TABLE II

| Runs | % Phenindamine | % Filler | Filler Used | Acetaminophen | % Pseudoephedrine | Stable |
|---|---|---|---|---|---|---|
| Comparative I | 29.41 | 70.59 | Microcrystalline Cellulose | — | — | No |
| Comparative J | 43.86 | 56.14 | Carboxymethyl Starch | — | — | No |
| Comparative K | 32.47 | 67.53 | Hydroxypropyl Cellulose | — | — | Yes |
| Comparative L | 11.11 | 88.89 | Calcium Carbonate | — | — | Yes |
| Comparative M | 3.70 | — | — | 96.30 | — | No |
| Comparative N | 4.31 | — | — | 95.69 | — | No |
| Comparative O | 29.41 | — | — | — | 70.59 | No |
| Comparative P | 11.11 | 88.89 | Calcium Sulfate | — | — | Yes |
| Comparative Q | 7.20 | 28.82 | Calcium Sulfate | 63.98 | — | No |
| Comparative R | 2.50 | 19.98 | Calcium Sulfate | 71.53 | 5.99 | No |
| Comparative S | 11.11 | 88.89 | Starch | — | — | Yes |
| Comparative T | 6.41 | 93.59 | Starch | — | — | No |
| Comparative U | 6.41 | 22.36 | Starch | 71.23 | — | No |
| Comparative V | 6.41 | 78.21 | Starch | — | 15.38 | No |

EXAMPLE III

Inventive 4

This example demonstrates the formation of tablets using the leachable wax matrix of this invention.

The product of Example I Inventive Run 3 was dry blended with acetaminophen and pseudoephedrine. Tablets were compressed at 2 tons pressure, maximum. The tablet contained 23% phenindamine, 5.5% pseudoephedrine and 58% acetaminophen.

Tablets were stored at 25° C., 45° C. and 60° C. for one month and the phenindamine content determined by HPLC assay. The tablets exhibited good stability and no isomerization at 25° C. and 45° C. with slight conversion at 60° C. (15%). The tablet exhibited an 88.8% dissolution when performed according to USP Dissolution Apparatus Method II at 37° C., 50 RPM for 1 hour in water.

The invention being thus described, it will be obvious that the same may be varied in many ways. Such variations are not to be regarded as a departure from the spirit and scope of the invention and all such modifications are intended to be included within the scope of the following claims.

What is claimed is:

1. A pharmaceutical composition of matter for use in the treatment of sinus, allergy, and cold symptoms, which comprises an effective amount of a pharmaceutically acceptable salt of phenindamine entrapped in a leachable non-toxic wax matrix in combination with an effect amount for use in the treatment of sinus, allergy and cold symptoms of at least one analgesic non-entrapped in said wax matrix, said phenindamine salt being present in the wax matrix in an amount of at lest one part leachable wax matrix to one part phenindamine salt, said wax matrix protecting said phenindamine salt to prevent contact with any phenindamine isomerization agent in said composition to prevent isomerization of said phenindamine salt to isophenindamine.

2. The composition of claim 1 wherein the leachable non-toxic wax matrix contains a leachable filler.

3. The composition of claims 2 wherein the leachable filler is selected from the group consisting of calcium sulfate, calcium carbonate, calcium phosphate, sugar, starch and mixtures thereof.

4. The composition in claim 1 wherein the pharmaceutically acceptable salts of phenindamine are selected from the group consisting of citrate, hydrobromide, hydrochloride, maleate, succinate, sulfate, tartrate, and mixtures thereof.

5. The composition of claim 1 wherein the leachable non-toxic wax matrix is selected from the group consisting of hydrogenated vegetable oil, beeswax, carnauba wax, paraffin, candelillia, ozokerite, and mixtures thereof.

6. The composition of claim 1 wherein the wax matrix contains about 36 to about 60% wax, about 4 to about 40% phenindamine salt, and about 10 to about 60% filler as the leachable component.

7. The composition of claim 1 wherein the analegesic materials are selected from the group consisting of acetaminophen, aspirin, salicylamide, phenacetin, ibuprofin and mixtures thereof.

8. The composition of claim 5 wherein the wax matrix has a melting point above about 35° C.

9. A method for the treatment of sinus, allergy and cold symptoms in the mammalian organism which comprises oral administration of the pharmaceutical composition of claim 2.

10. A method in the treatment of sinus, allergy and cold symptoms in the mammalian organism which comprises oral administration of the pharmaceutical composition of claim 1.

* * * * *